United States Patent [19]

Hashiba et al.

[11] Patent Number: 5,206,431

[45] Date of Patent: Apr. 27, 1993

[54] PROCESS FOR PRODUCING METHACRYLIC ACID

[75] Inventors: Hideto Hashiba; Shigeru Ohno; Ikuo Kurimoto, all of Himeji; Yukio Aoki, Hyogo, all of Japan

[73] Assignee: Nippon Shokubai Kagaku Kogyo Co., Ltd., Osaka, Japan

[21] Appl. No.: 928,184

[22] Filed: Aug. 14, 1992

Related U.S. Application Data

[63] Continuation of Ser. No. 651,951, Feb. 7, 1991, abandoned.

[51] Int. Cl.$^5$ .............................................. C07C 51/21
[52] U.S. Cl. .................................. 562/534; 562/535; 562/599
[58] Field of Search ................ 562/534, 599, 535, 598

[56] References Cited

U.S. PATENT DOCUMENTS

| | | | |
|---|---|---|---|
| 4,558,028 | 10/1985 | Tsuneki et al. | 502/211 |
| 4,595,778 | 6/1986 | Duembgen et al. | 560/208 |
| 4,837,360 | 6/1989 | Kadowaki et al. | 562/546 |

FOREIGN PATENT DOCUMENTS

| | | |
|---|---|---|
| 2538382 | 6/1984 | France . |
| 59-20243 | 2/1984 | Japan . |
| 59-115750 | 7/1984 | Japan . |
| 63-38331 | 7/1988 | Japan . |
| 1360819 | 7/1974 | United Kingdom . |

OTHER PUBLICATIONS

Patent Abstracts of Japan, (Unexamined applns. C Field, vol. 8, No. 106, May 18, 1984.
English Abstract of Japanese Laid-Open Patent Publication No. 59-20243/1984.

*Primary Examiner*—Arthur C. Prescott
*Attorney, Agent, or Firm*—Sherman and Shalloway

[57] ABSTRACT

A process for producing methacrylic acid, which comprises filling a plurality of catalysts of different activities into a plurality of reaction zones which have been formed in each of the reaction tubes of a fixed bed multi-tubular reactor by dividing said reaction tube into two or more portions in the direction of tubular axis, so that the activity of catalyst is higher as the reaction zone is closer to the outlet of the reaction tube, and introducing into the reaction zones containing the catalysts at least one compound selected from methacrolein, isobutyl aldehyde and isobutyric acid to oxidize the at least one compound with molecular oxygen or a molecular oxygen-containing gas.

3 Claims, No Drawings

PROCESS FOR PRODUCING METHACRYLIC ACID

This application is a continuation of application Ser. No. 07/651,951, filed Feb. 7, 1991, now abandoned.

The present invention relates to a process for producing methacrylic acid. More particularly, the present invention relates to a process for producing methacrylic acid by oxidizing at least one compound as a starting material, selected from methacrolein, isobutyl aldehyde and isobutyric acid, with molecular oxygen or a molecular oxygen-containing gas in the presence of oxidation catalysts.

A number of proposals have been made on the catalyst used in production of methacrylic acid by the vapor phase catalytic oxidation reaction of methacrolein or the vapor phase catalytic oxidative dehydrogenation reaction of isobutyl aldehyde or isobutyric acid. (In the present invention, the above oxidation reaction and oxidative dehydrogenation reaction are referred generically to simply as "oxidation reaction", unless otherwise specified.) These proposals relate mainly to the selection of (a) the components constituting the catalyst and (b) their ratio.

The above oxidation reaction is a highly exothermic reaction. Therefore, in the reaction, heat build-up in the catalyst layer is large; particularly in the abnormally hot local areas called "hot spots", product yield is low due to an excessive oxidation reaction, deterioration of catalyst takes place, and catalyst life is influenced greatly. Accordingly, heat build-up in hot spots is a serious problem in the industrial practice of the above oxidation reaction. This heat build-up in hot spots tends to be striking particularly when the concentration of material gas is increased or the space velocity is made larger (such reaction conditions are hereinafter referred to as "high-load reaction conditions" in some cases) in order to enhance the productivity; as a result, the reaction conditions of the oxidation reaction are fairly restricted currently.

Hence, minimization of heat-up in hot spots is very important for industrial production of methacrylic acid at a high yield as well as for reduction of catalyst deterioration and resultant stable operation over a long period. Prevention of heat build-up in hot spots is particularly important in molybdenum-containing catalysts because the molybdenum component causes easy sublimation.

Various proposals have hitherto been made in order to suppress heat build-up in hot spots. For example, Japanese Laid-Open Patent Publication No. 115750/1984 proposes the use of a ring-shaped catalyst. The document describes that in the production of methacrylic acid, the change of catalyst shape from a conventional spherical or cylindrical shape to a ring shape can suppress heat build-up in hot spots and accordingly an excessive oxidation reaction and is very effective for the improvement of product yield. This method certainly has an effect of reducing the thermal load for catalyst, but gives no sufficient results under high-load reaction conditions.

It is known in Japanese Patent Publication No. 38331/1988 that in the process for producing acrolein and acrylic acid from propylene, a plurality of catalysts of different activities are filled into a plurality of reaction zones formed by dividing a reactor and an oxidation reaction is effected in the reaction zones containing said caatalysts.

In the reaction for producing methacrylic acid by, for example, oxidation of methacrolein, methacrolein having a methyl group at the α-position is used as a starting material, as compared with the use of acrolein in acrylic acid production. Therefore, in the oxidation of methacrolein, there occurs many side reactions caused by the presence of methyl group, such as parallel reactions, successive reactions and the like, producing a nmumber of by-products in large amounts. Further, the heat generated in the reaction for producing methacrylic acid from methacrolein is larger than that for producing acrylic acid from acrolein; this aggravates the heat build-up catalyst layer and promotes the formation of by-products by side reactions. Furthermore, methacrylic acid is unstable as compared with acrylic acid and easily gives rise to so-called "post-reactions" such as autooxidation and the like, worsening the product yield.

As described above, the reaction for producing methacrylic acid is complex as compared with the reaction for producing acrylic acid, making it difficult to obtain an intended product at a high yield. Therefore, the application of the techniques obtained in the production of acrolein, acrylic acid, etc., to the production of methacrylic acid have not been sufficiently effective, and further study has been necessary in order to develop an improved catalyst or improved process for producing methacrylic acid.

Japanese Laid-Open Patent Publication No. 20243/1984 proposes a process for producing methacrylic acid from methacrolein by the combination use of catalysts of different phosphorus contents. In this document, it is proposed to fill a catalyst of higher phosphorus content into the material gas inlet portion of the reactor to stabilize the catalyst system, based on the finding that the molybdenum and phosphorus-containing catalyst effective for production of methacrylic acid has, for the most part, a heteropoly-acid type structure of low heat resistance and causes severe volatilization of phosphorus at the material gas inlet portion of the reactor.

As described above, there was proposed a process for producing methacrylic acid from methacrolein by the combination use of catalysts of different phosphorus contents.

It was found by the present inventors as well that the volatilization of phosphorus takes place partially at the material gas inlet portion of the reactor during the reaction for methacrylic acid production from methacrolein. However, filling of a catalyst of high phosphorus content at the material gas inlet portion as a measure for the phosphorus volatilization is not sufficient for the stabilization of total catalyst system, because it is known by literatures that many of catalysts containing molybdenum and phosphorus as essential components, suitable for methacrylic acid production have a heteropoly-acid type structure but this structure has low heat resistance and is easily decomposed at 400–450° C.

The decomposition of heteropoly-acid type structure invites reduction in methacrolein conversion as well as in methacrylic acid selectivity. Elevation of reaction temperature in order to maintain the conversion invites heat generation owing to reduction in methacrylic acid selectivity, i.e. increase in $CO_2$ selectivity; this heat generation slowly increases heat build-up in catalyst layer; it accelerates the decomposition of heteropoly-acid type structure; finally, the heat build-up cannot be controlled and the reaction becomes uncontrolleable, making its continuation impossible.

Thus, heteropoly-acid type catalysts are difficult to predict their life, and suddenly show a last-stage phenomenon. This is unique to the catalysts but is a very disadvantageous property from the standpoint of stable operation for industrial production of methacrylic acid.

Therefore, when methacrylic acid is produced using a catalyst of heteropoly-acid type structure, it is necessary to pay an utmost attention to the dispersion of the heat accumulated in the catalyst layer, whereby the extension of catalyst life and the stable operation for industrial production of methacrylic acid become possible.

An object of the present invention is to provide a process for producing methacrylic acid at a high yield by oxidizing at least one compound selected from methacrolein, isobutyl aldehyde and isobutyric acid.

Another object of the present invention is to provide a process for producing methacrylic acid by oxidizing at least one compound selected from methacrolein, isobutyl aldehyde and isobutyric acid, wherein the heat build-up in hot spots in catalyst layer is suppressed to increase the yield of methacrylic acid and the deterioration of catalyst is prevented to enable the stable use of catalyst over a long period.

Still another object of the present invention is to provide a process for producing methacrylic acid by oxidizing, under high-load reaction conditions, at least one compound selected from methacrolein, isobutyl aldehyde and isobutyric acid, wherein the heat build-up in hot spots in catalyst layer is suppressed to increase the yield of methacrylic acid, the deterioration of catalyst is prevented to enable the stable use of catalyst over a long period, and thereby productivity is improved significantly.

The researches by the present inventors revealed that the above objects can be achieved by, in oxidizing at least one compound selected from methacrolein, isobutyl aldehyde and isobutyric acid, preparing a plurality of oxidation catalysts of different activities and filling these catalysts into a plurality of reaction zones which have been formed in a reaction tube by dividing the reaction tube in the direction of tubular axis, so that the activity of catalyst is higher as the catalyst zone is closer to the outlet of reaction tube.

According to the present invention, there is provided a process for producing methacrylic acid, which comprises filling a plurality of catalysts of different activities into a plurality of reaction zones which have been formed in each of the reaction tubes of a fixed bed multi-tubular reactor by dividing said reaction tube into two or more portions in the direction of tubular axis, so that the activity of catalyst is higher as the reaction zone is closer to the outlet of the reaction tube, and introducing into the reaction zones containing the catalysts at least one compound selected from methacrolein, isobutyl aldehyde and isobutyric acid to oxidize the at least one compound with molecular oxygen or a molecular oxygen-containing gas.

The present invention is hereinafter described in detail.

In the present invention, a plurality of reaction zones are formed in each of the reaction tubes of a fixed bed multi-tublar reactor by dividing the reaction tube into two or more portions in the direction of tubular axis. In this case, the more the reaction zones, the easier is the control of the temperature distribution in the catalyst zones; industrially, however, 2 or 3 reaction zones are enough to obtain intended effects. The detail of division of each reaction tube into reaction zones cannot be determined by a general rule because it varies depending upon the composition, shape, etc. of the catalyst to be filled into each reaction zone; therefore, it should be determined so that the most appropriate activity and selectivity can be obtained overall.

In the present invention, a plurality of oxidation catalysts of different activities are filled into said plurality of reaction zones so that the activity of catalyst is higher as the reaction zone is closer to the outlet of reaction tube. That is, the catalyst of lowest activity is filled into the reaction zone having a material gas inlet, and the catalyst of highest activity is filled into the reaction zone having an outlet. By employing such arrangement of catalysts, heat build-up in hot spots can be suppressed and methacrylic acid can be obtained at a high selectivity.

Incidentally, the "activity" used in the present invention refers to the conversion of starting material.

The catalysts used in the present invention can be any conventionally known oxidation catalysts; however, particularly preferable are compound oxides represented by the following general formula (I).

$$Mo_a P_b A_c B_d C_e O_x \qquad (I)$$

wherein Mo represents molybdenum (Mo); P represents phosphorus (P); A represents at least one element selected from arsenic (As), antimony (Sb), germanium (Ge), bismuth (Bi), zirconium (Zr), selenium (Se), cerium (Ce), copper (Cu), iron (Fe), chromium (Cr), nickel (Ni), manganese (Mn), cobalt (Co), tin (Sn), silver (Ag), zinc (Zn), palladium (Pd), rhodium (Rh) and tellurium (Te); B represents at least one element selected from vanadium (V), tungsten (W) and niobium (Nb); C represents at least one element selected from alkali metals [e.g. lithium (Li), sodium (Na), potassium (K), rubidium (Rb) and cesium (Cs)], alkaline earth metals [e.g. beryllium (Be), magnesium (Mg), calcium (Ca), strontium (Sr) and barium (Ba)] and thallium; 0 represents oxygen (0); a,b,c,d,e and x represent the atom numbers of Mo, P, A, B, C and 0, respectively; when a is 12, b is 0.5-4, c is 0.001-5, d is 0.001-4 and e is 0.001-4; and x is a value determined by the oxidation state of each element.

The catalysts of different activities, represented by the general formula (I) can be prepared by, for example, the following methods.

(1) Changes the kinds and/or amounts of the group A elements in the general formula (1).

(2) Changes the kinds and/or amounts of the group B elements in the general formula (1).

(3) Changes the kinds and/or amounts of the group C elements in the general formula (1).

(4) Changes the kinds and/or amounts of the elements of at least two groups selected from the group A, the group B and the group C.

The amounts of the group A elements, the group B elements and the group C elements are changed within the ranges of the atom numbers c, d and e specified in the general formula (I).

The preparation method of the catalysts used in the present invention as well as their raw materials are not particularly restricted, and the present catalysts can be prepared using the methods and materials generally used in the preparation of such catalysts.

The present catalysts can be used, for example, as molded catalysts obtained by an ordinary molding method such as extrusion molding method, tablet molding method or the like, or as supported catalysts obtained by allowing an ordinary inactive carrier (e.g. silicon carbide, alumina, zirconium oxide, titanium oxide) to support a catalyst component [e.g. a compound oxide represented by the general formula (I)].

The types of the different catalysts filled into a plurality of reaction zones may be the same or different. When the number of the reaction zones is, for example, 2, it is possible to fill a supported catalyst into a reaction zone functioning also as a material gas inlet and fill a molded catalyst into a reaction zone also functioning as an outlet.

The shapes of the catalysts used in the present invention has no particular restriction, either, and can be spherical, columnar, ring-shaped, etc. The use of ring-shaped catalysts can give various advantages such as prevention of heat build-up in hot spots, increased yield, prevention of catalyst deterioration, reduced pressure drop in catalyst layer, and the like. Therefore, ring-shaped catalysts can be preferably used in the present invention. The preferable dimensions of the ring-shaped catalysts are such that the outside diameter is 3-10 mm, the length is 0.5-2 times the outside diameter, and the inside diameter (the diameter of the through-hole formed in the length direction) is 0.1-0.7 time the outside diameter.

The shapes of the different catalysts filled into a plurality of reaction zones may be the same or different. When the number of the reaction zones is, for example, 2, better results are obtained by filling a ring-shaped catalyst into a reaction zone functioning also as a material gas inlet and a pellet-shaped catalyst into a reaction zone functioning also as an outlet.

The starting material used in the present invention is at least one compound selected from methacrolein, isobutyl aldehyde and isobutyric acid. As described above, methacrolein gives methacrylic acid by an oxidation reaction, and isobutyl aldehyde or isobutyric acid gives methacrylic acid by an oxidative dehydrogenation reaction.

The oxidation reaction in the present invention may be effected by an ordinary single-pass method or a recycle method. The reaction conditions have no particular restriction, and the oxidation reaction can be effected under the conditions generally employed in similar reactions. For example, a mixed gas consisting of 1-10 % by volume of a starting material, 3-20 % by volume of molecular oxygen, 0-60 % by volume of steam, 20-80 % by volume of an inert gas (e.g. nitrogen, carbon dioxide), etc. is introduced into a catalyst layer consisting of the present catalysts and subjected to a reaction at a temperature range of 250-450° C. at pressure of normal pressure to 10 atm. at a space velocity of 300-5,000 $hr^{-1}$.

In the present process, far more advantageous results can be obtained under high-load reaction conditions (e.g. higher material concentration, higher space velocity) than in conventional processes, whereby higher productivity can be obtained.

In the present invention, various meritorious effects such as mentioned below can be obtained by filling a plurality of catalysts of different activities into a plurality of reaction zones so that the activity of catalyst is higher as the reaction zone is closer to the outlet of reaction tube.

(a) Methacrylic acid can be obtained at a high yield.
(b) Heat build-up in hot spots can be suppressed effectively.
(c) The excessive oxidation reaction in hot spots can be prevented and methacrylic acid can be obtained at a high yield.
(d) Catalyst deterioration due to thermal load can be prevented and stable use of catalyst over long period is possible.
(e) Methacrylic acid can be obtained at a high yield even under high-load reaction conditions (e.g. high material concentration, high space velocity), whereby productivity can be increased significantly.

Further, the following effect can additionally be obtained by the use of ring-shaped catalyst.

(f) Pressure drop in catalyst layer is reduced, whereby electricity consumption can be decreased.
(g) As shown in the present invention, when the reaction for methacrylic acid production is effected using two or more catalysts of different activities in combination, it is possible to disperse the load of reaction on the entire portion of the catalyst layer. Consequently, the local heat load resulting from the reaction can be minimized and, moreover, reduction in catalyst activity can be made smaller; therefore, it is not necessary to increase the reaction temperature vainly, which is very advantageous to the heteropoly-acid type catalyst of low heat resistance and makes possible the extension of catalyst life.

Thus, the process of the present invention is very useful for industrial production of methacrylic acid.

The present invention is hereinafter described in more detail by way of Examples.

In the Examples, conversion, selectivity and one-pass yield are defined by the following formulas.

---

Conversion (mole %) =
(moles of starting material reacted) ÷
(moles of starting material fed) × 100
Selectivity (mole %) =
(moles of methacrylic acid formed) ÷ (moles of starting material reacted) × 100
One-pass yield (mole %) =
(moles of methacrylic acid formed) ÷ (moles of starting material fed) × 100

---

EXAMPLE 1

To 40 l of heated deionized water were added 8,830 g of ammonium paramolybdate and 531 g of ammonium metavanadate. The resulting mixture was stirred to obtain an aqueous solution. To this solution were added 625 g of orthophosphoric acid (85 wt. %), an aqueous solution obtained by dissolving 812 g of cesium nitrate in 9 l of deionized water, and 30 g of powdery antimony trioxide in this order. The resulting mixture was concentrated by heating with stirring.

The resulting slurry was dried at 250° C. for 15 hours, followed by grinding. The resulting particles were wetted with water to an appropriate degree and then molded into pellets of 5 mm in diameter and 6 mm in length using a screw type extruder. The pellets were dried and calcined in air at 400° C. for 3 hours to prepare a pellet catalyst (1).

The catalyst (1) had the following composition when expressed as an atomic ratio excluding oxygen.

$$Mo_{12}P_{1.3}V_{1.09}Cs_{1.0}Sb_{0.05}$$

A pellet catalyst (2) was prepared in the same manner as for the catalyst (1) except that the amount of antimony trioxide used was changed to 425 g.

The catalyst (2) had the following composition when expressed as an atomic ratio excluding oxygen.

$$Mo_{12}P_{1.3}V_{1.09}Cs_{1.0}Sb_{0.7}$$

750 ml of the catalyst (1) was filled into the material gas inlet portion of a steel-made reaction tube of 25.4 mm in inside diameter, and sucessively 750 ml of the catalyst (2) was filled into the outlet portion of the same reaction tube.

Into this catalyst layer was introduced a mixed gas having the following composition, obtained by subjecting isobutylene to gas phase catalytic oxidation in the presence of a multi-element catalyst of Mo-Co-W-Fe oxide type, to effect a reaction at a reaction temperature of 290° C. at a space velocity of 1,200 $hr^{-1}$.

| | |
|---|---|
| Methacrolein | 3.5% by volume |
| Isobutylene | 0.04% by volume |
| Methacrylic acid + acetic acid | 0.24% by volume |
| Steam | 20% by volume |
| Oxygen | 9% by volume |
| Others | 67.22% by volume |

The results are shown in Table 1.

COMPARATIVE EXAMPLE 1

A reaction was effected in the same manner as in Example 1 except that no catalyst (2) was used and only the catalyst (1) (1,500 ml) was filled.

The results are shown in Table 1.

COMPARATIVE EXAMPLE 2

A reaction was effected in the same manner as in Example 1 except that no catalyst (1) was used and only the catalyst (2) (1,500 ml) was filled.

The results are shown in Table 1.

COMPARATIVE EXAMPLE 3

A pellet catalyst (3) was prepared in the same manner as for the catalyst (1) of Example 1 except that the amount of antimony trioxide used was changed to 243 g.

The catalyst (3) had the following composition when expressed as an atomic ratio excluding oxygen.

$$Mo_{12}P_{1.3}V_{1.09}Cs_{1.0}Sb_{0.4}$$

A reaction was effected in the same manner as in Example 1 except that only the catalyst (3) (1,500 ml) was used.

The results are shown in Table 1.

In Table 1, when Example 1 is compared with Comparative Examples 1 and 2, Comparative Example 1 using a single layer of the catalyst (1) gives a very low activity, Comparative Example 2 using a single layer of the catalyst (2) gives a high activity but a low selectivity, and Comparative Examples 1 and 2 each gives a low yield; meanwhile, Example 1 using a combination of the catalyst (1) and the catalyst (2) gives a high yield and very good results.

Comparative Example 3 using a single layer of the catalyst (3) having an intermediate composition between those of the catalyst (1) and the catalyst (2) gives a low yield and a very large ΔT (temperature difference between reaction temperature and temperature of hot spots). Therefore, it is presumed that the use of this catalyst gives severe catalyst deterioration due to thermal load.

Thus, it can be said that the combination of the catalyst (1) and the catalyst (2) according to the present invention gives significantly superior results in yield and thermal load.

EXAMPLE 2

As reaction was effected in the same manner as in Example 1 except that as the catalyst (1) and the catalyst (2), there were used those obtained by molding into a ring shape having an outside diameter of 5 mm, a length of 6 mm and an inside diameter (a diameter of the through-hole formed in the length direction) of 1 mm.

The results are shown in Table 1.

COMPARATIVE EXAMPLE 4

A reaction was effected in the same manner as in Comparative Example 1 except that as the catalyst (1), there was used one obtained by molding into a ring shape having an outside diameter of 5 mm, a length of 6 mm and an inside diameter (a diameter of the through-hole formed in the length direction) of 1 mm.

The results are shown in Table 1.

COMPARATIVE EXAMPLE 5

A reaction was effected in the same manner as in Comparative Example 2 except that as the catalyst (2), there was used one obtained by molding into a ring shape having an outside diameter of 5 mm, a length of 6 mm and an inside diameter (a diameter of the through-hole formed in the length direction) of 1 mm.

The results are shown in Table 1.

COMPARATIVE EXAMPLE 6

A reaction was effected in the same manner as in Comparative Example 3 except that as the catalyst (3), there was used one obtained by molding into a ring shape having an outside diameter of 5 mm, a length of 6 mm and an inside diameter (a diameter of the through-hole formed in the length direction) of 1 mm.

The results are shown in Table 1.

In all of Example 2 and Comparative Examples 4–6, the use of ring-shaped catalyst gave a higher yield and a lower ΔT. However, the combination use of the catalyst (1) and the catalyst (2) gave better results in yield and ΔT than the use of the catalyst (1), (2) or (3) alone.

EXAMPLE 3

A reaction was effected in the same manner as in Example 1 except that the catalyst (1) was molded so as to have a ring shape having an outside diameter of 5 mm, a length of 6 mm and an inside diameter (a diameter of the through-hole formed in the length direction) of 1 mm.

The results are shown in Table 1.

As is clear from Table 1, Example 3 using a ring catalyst (1) in the inlet portion of a reaction tube gave a higher yield and a lower ΔT. That is, the combination use of catalysts different not only in activity but also in shape gives better results.

EXAMPLE 4

The reaction of Example 3 was effected for 4,000 hours. The results after 4,000 hours are shown in Table 1.

Activity reduction during the period was very small and yield reduction was substantially negligible. That is, the combination use of the catalysts of Example 3 enables very stable operation over a long period.

COMPARATIVE EXAMPLE 7

The reaction of Comparative Example 3 was effected for 4,000 hours. The results after 4,000 hours are shown in Table 1.

Activity reduction and yield reduction were both large as compared with those in Example 4, and the catalyst used in Comparative Example 7 had a problem in stability.

EXAMPLE 5

A reaction was effected in the same manner as in Example 2 except that the reaction temperature was changed to 300° C. and the space velocity was changed to 1,500 $hr^{-1}$.

The results are shown in Table 1.

COMPARATIVE EXAMPLE 8

A reaction was effected in the same manner as in Comparative Example 4 except that the reaction temperature was changed to 300° C. and the space velocity was changed to 1,500 $hr^{-1}$.

The results are shown in Table 1.

COMPARATIVE EXAMPLE 9

A reaction was effected in the same manner as in Comparative Example 6 except that the reaction temperature was changed to 300° C. and the space velocity was changed to 1,500 $hr^{-1}$.

The results are shown in Table 1.

The comparison of Example 5 with Comparative Examples 8-9 indicates that the combination use of the catalyst (1) and the catalyst (2) gives a higher activity and a higher yield even under a high space velocity condition than the use of the catalyst (1) or (3) alone.

EXAMPLE 6

A reaction was effected in the same manner as in Example 2 except that the concentrations of methacrolein and nitrogen in the material gas was changed to 4.0 % by volume and 66.72 % by volume, respectively.

The results are shown in Table 1.

COMPARATIVE EXAMPLE 10

A reaction was effected in the same manner as in Comparative Example 4 except that the concentrations of methacrolein and nitrogen in the material gas was changed to 4.0% by volume and 66.72% by volume, respectively.

The results are shown in Table 1.

COMPARATIVE EXAMPLE 11

A reaction was effected in the same manner as in Comparative Example 6 except that the concentrations of methacrolein and nitrogen in the material gas was changed to 4.0 % by volume and 66.72 % by volume, respectively.

The results are shown in Table 1.

The comparison of Example 6 with Comparative Examples 10-11 indicates that the combination use of the catalyst (1) and the catalyst (2) gives a higher activity and a higher yield even when the methacrolein concentration in material gas is increased, than the use of the catalyst (1) or (3) alone. Increase in ΔT is fairly small in the combination use of the catalyst (1) and the catalyst (2), as compared with the using the catalyst (1) or (3) alone; therefore, the above catalyst combination is thought to be effective for minimization of catalyst deterioration due to thermal load.

EXAMPLE 7

A reaction was effected in the same manner as in Example 2 except that there was used, as the material gas, a mixed gas consisting of 5 % by volume of isobutyl aldehyde, 12.5 % by volume of oxygen, 10 % by volume of steam and 72.5.% by volume of nitrogen and that the space velocity was changed to 800 $hr^{-1}$ and the reaction temperature was changed to 280° C.

The results are shown in Table 2.

COMPARATIVE EXAMPLE 12

A reaction was effected in the same manner as in Comparative Example 4 except that there was used, as the material gas, a mixed gas consisting of 5% by volume of isobutyl aldehyde, 12.5 % by volume of oxygen, 10% by volume of steam and 72.5 % by volume of nitrogen and that the space velocity was changed to 800 $hr^{-1}$ and the reaction temperature was changed to 280° C.

The results are shown in Table 2.

COMPARATIVE EXAMPLE 13

A reaction was effected in the same manner as in Comparative Example 6 except that there was used, as the material gas, a mixed gas consisting of 5% by volume of isobutyl aldehyde, 12.5% by volume of oxygen, 10% by volume of steam and 72.5% by volume of nitrogen and that the space velocity was changed to 800 $hr^{-1}$ and the reaction temperature was changed to 280° C.

The results are shown in Table 2.

EXAMPLE 8

A reaction was effected in the same manner as in Example 2 except that there was used, as the material gas, a mixed gas consisting of 5% by volume of isobutyric acid, 10% by volume of oxygen, 10% by volume of steam and 75% by volume of nitrogen and that the space velocity was changed to 2,000 $hr^{-1}$ and the reaction temperature was changed to 280° C.

The results are shown in Table 3.

COMPARATIVE EXAMPLE 14

A reaction was effected in the same manner as in Comparative Example 4 except that there was used, as the material gas, a mixed gas consisting of 5% by volume of isobutyric acid, 10% by volume of oxygen, 10% by volume of steam and 75% by volume of nitrogen and that the space velocity was changed to 2,000 $hr^{-1}$ and the temperature was changed to 280° C.

The results are shown in Table 3.

COMPARATIVE EXAMPLE 15

A reaction was effected in the same manner as in Comparative Example 6 except that there was used, as the material gas, a mixed gas consisting of 5% by volume of isobutyric acid, 10% by volume of oxygen, 10% by volume of steam and 75% by volume of nitrogen and that the space velocity was changed to 2,000 hr$^{-1}$ and the reaction temperature was changed to 280° C.

The results are shown in Table 3.

EXAMPLE 9

To 40 l of heated deionized water were added 8,830 g of ammonium paramolybdate and 731 g of ammonium metavanadate. The resulting mixture was stirred to obtain an aqueous solution.

To this solution were added 523 g of orthophosphoric acid (85 wt. %), an aqueous solution obtained by dissolving 337 g of potassium nitrate and 569 g of cesium nitrate in 9 l of deionized water, and 43.6 g of germanium oxide in this order. The resulting mixture was concentrated by heating with stirring.

The resulting slurry was dried at 250° C. for 15 hours. The subsequent procedure was the same as in Example 1, to prepare a pellet catalyst (4).

The catalyst (4) had the following composition when expressed as an atomic ratio excluding oxygen.

$Mo_{12}P_{1.09}V_{1.5}Cs_{0.7}K_{0.8}Ge_{0.1}$

A pellet catalyst (5) was prepared in the same manner as for the catalyst (4) except that the amount of ammonium metavanadate used was changed to 341 g and the amount of potassium nitrate used was changed to 126 g. The catalyst (5) had the following composition when expressed as an atomic ratio excluding oxygen.

$Mo_{12}P_{1.09}V_{0.7}Cs_{0.7}K_{0.3}Ge_{0.1}$ 750 ml of the catalyst (4) was filled into the material gas inlet portion of a steel-made reaction tube of 25.4 mm in inside diameter, and sucessively 750 ml of the catalyst (5) was filled into the outlet portion of the same reaction tube, to effect a reaction in the same manner as in Example 1.

The results are shown in Table 4.

EXAMPLE 10

To 40 l of heated deionized water were dispersed 4,802 g of molybdenum trioxide, 276 g of vanadium pentozide, 22.1 g of copper oxide, 44.4 g of iron oxide, 41.9 g of tin oxide and 349.4 g of orthophosphoric acid (85 wt. %). The resulting despersion was stirred for about 3 hours with heating. Then, 427.3 g of rubidium hydroxide was added and the resulting mixture was stirred for about 3 hours under refluxing, to obtain a suspension.

The suspension was concentrated by heating with stirring, to prepare a slurry. The slurry was dried a 250° C. for 15 hours. The subsequent procedure as the same as in Example 1, to prepare a pellet catalyst (6) having a diameter of 5 mm and a length of 6 mm.

The catalyst (6) had the following composition when expressed as an atomic ratio excluding oxygen.

$Mo_{12}P_{1.09}V_{1.09}Cu_{0.1}Rb_{1.5}Fe_{0.2}Sn_{0.1}$

A pellet catalyst (7) was prepared in the same manner as for the catalyst (6) except that the amount of copper oxide used was changed to 66.3 g and the amount of the rubidium hydroxide used was changed to 142.4 g.

The catalyst (7) had the following composition when expressed as an atomic ratio excluding oxygen.

$Mo_{12}P_{1.09}V_{1.09}Cu_{0.3}Rb_{0.5}Fe_{0.2}Sn_{0.1}$ 750 ml of the catalyst (6) was filled into the material gas inlet portion of a steel-made reaction tube of 25.4 mm in inside diameter, and successively 750 ml of the catalyst (7) was filled into the outlet portion of the same reaction tube, to effect a reaction in the same manner as in Example 1.

The results are shown in Table 4.

EXAMPLE 11

4,770 g of ammonium molybdate was dissolved in 18 l of water.

234 g of orthophosphoric acid (85 wt. %) was diluted with 1,350 ml of water, and 20.1 g of arsenous acid was dissolved therein. The resulting solution was added to the aqueous ammonium molybdate solution prepared above. The resulting mixture was sufficiently stirred with heating to effect aging, whereby a reaction product of phosphorous molybdenum and aresenic was obtained as a precipitate.

234 g of orthophosphoric acid (85 wt.%) was diluted with 1,350 ml of water. Thereto was added 184.4 g of vanadium pentoxide. The mixture was stirred with heating to vaporize water, whereby a yellow complex was formed. This complex was added to the above precipitate (reaction product of phosphorous molybdenum and arsenic). The mixture was added to an aqueous solution obtained by dissolving 34.4 g of silver nitrate and 120.6 g of zinc nitrate hexahydrate, to effect sufficient aging. Then, there was added an aqueous solution obtained by dissolving 370.9 g of barium nitrate in 2 l of water. The resulting mixture was concentrated by heating with stirring, to obtain a slurry.

The slurry was dried at 250° C. for 15 hours, followed by grinding. The resulting particles were wetted with water to an appropriate degree and then molded into rings of 5 mm in outside diameter, 6 mm in length and 1.5 mm in inside diameter (diameter of the through-hole formed in the length direction) using a screw type extruder. The rings were dried and calcined in air at 400° C. for 3 hours to prepare a ring catalyst (8).

The catalyst (8) had the following composition when expressed as an atomic excluding oxygen.

$Mo_{12}P_2V_1As_{0.1}Ba_{0.7}Ag_{0.1}Zn_{0.2}$

A slurry was obtained in the same manner as for the catalyst (8) except that the amounts of arsenous acid used was changed to 140.4 g, the amount of barium nitrate used was changed to 53 g, and 1,100 g of pyridine and 2.2 l of nitric acid (sp. gr.=1.38) were newly added together with arsenous acid.

The slurry was dried at 250° C. for 15 hours, followed by grinding. The resulting particles were wetted with water to an appropriate degree and then molded into pellets of 5 mm in diameter and 6 mm in length using a screw type extruder. The pellets were dried and calcined in the nitrogen at 400° C. for 3 hours and then in the air at 400° C. for 3 hours to prepare a pellet catalyst (9).

The catalyst (9) had the following composition when expressed as an atomic ratio excluding oxygen.

$Mo_{12}P_2V_1As_{0.7}Ba_{0.1}Ag_{0.1}Zn_{0.2}$ 750 ml of the catalyst (8was filled into the material gas inlet portion of a steel-made reaction tube of 25.4 mm in inside diameter, and successively 750 ml of the catalyst (9) was filled into the outlet portion of the same reaction tube, to effect a reaction in the same manner as in Example 1.

The results are shown in Table 4.

EXAMPLE 12

To 35 l of heated deionized water were added 4,320 g of molybdenum trioxide, 227.4 g of vanadium pentoxide and 432.5 g of orthophosphoric acid (85 wt. %). The resulting mixture was stirred for 24 hours with heating. Thereto were added 43 g of powdery cerium oxide, 118.1 g of calcium nitrate and 258 g of rubidium nitrate. The resulting mixture was concentrated by heating with stirring.

The resulting clay-like substance was dried at about 100° C. for 4 hours and then ground. To the resulting particles were added 133.7 g of zirconium nitrate and 72.8 g of cobalt nitrate, and they were mixed sufficiently. Water was added thereto and sufficient kneading was effected. The kneaded substance was molded into rings of 5 mm in outside diameter, 6 mm in length and 1.5 mm in inside diameter (diameter of the through-hole formed in the length direction). The rings were dried and calcined in an air current at 400° C. for 3 hours, to obtain a ring catalyst (10).

The catalyst (10) had the following composition when expressed as an atomic ratio excluding oxygen.

$Mo_{12}P_{1.5}V_1Rb_{0.7}Ca_{0.2}Ce_{0.1}Zr_{0.2}Co_{0.1}$

A pellet catalyst (11) was obtained in the same manner as for the catalyst (10) except that the amount of cerium oxide used was changed to 387.4 g and the amount of zirconium nitrate was changed to 66.8 g and that the kneaded substance was molded into pellets of 5 mm in diameter and 6 mm in length.

The catalyst (11) had the following composition when expressed as an atomic ratio excluding oxygen.

$Mo_{12}P_{1.5}V_1Rb_{0.7}Ca_{0.2}Ce_{0.9}Zr_{0.1}Co_{0.1}$ 750 ml of the catalyst (10was filled into the material gas inlet portion of a steel-made reaction tube of 25.4 mm in inside diameter, and successively 750 ml of the catalyst (11) was filled into the outlet portion of the same reaction tube, to effect a reaction in the same manner as in Example 1.

The results are shown in Table 4.

EXAMPLE 13

To 20 l of heated deionized water were added 5,088 g of ammonium paramolybdate and 306.2 g of ammonium metavanadate. The resulting mixture was stirred to obtain a solution. To this solution were added 301.8 g of orthophosphoric acid (85 wt. %), an aqueous solution obtained by dissolving 254.1 g of strontium nitrate and 55.3 g of palladium nitrate in 3 l of deionized water, 116.5 g of powdery bismuth nitrate, 188.1 g of powdery ammonium tungstate, and an aqueous solution obtained by dissolving 24 g of chromic anhydride and 26.6 g of selenium dioxide in 3 l of deionized water, in this order. The resulting mixture was heated with stirring, to effect aging.

In the resulting suspension was immersed 1,600 ml of a carrier consisting of spherical α-alumina of 5 mm in diameter. The system was heated to a predetermined temperature with stirring, to allow the carrier to support the catalyst active component. The system was then calcined in an air current at 400° C. for 3 hours to obtain a supported catalyst (12).

The compound oxide of this catalyst (12) had the following composition when expressed as an atomic ratio excluding oxygen.

$Mo_{12}P_{1.09}V_{1.09}W_{0.3}K_{0.8}Sr_{0.5}Bi_{0.1}Se_{0.1}Cr_{0.1}Pd_{0.1}$

The amount of the compound oxide supported was 20 g per 100 ml of the carrier.

A slurry was prepared in the same manner as for the catalyst (12) except that the amount of strontium nitrate was changed to 50.8 g and the amount of ammonium tungstate used was changed to 438.9 g. The subsequent procedure was the same as in Example 1 to obtain a pellet catalyst (13) of 5 mm in outside diameter and 6 mm in length.

The catalyst (13) had the following composition when expressed as an atomic ratio excluding oxygen.

$Mo_{12}P_{1.09}V_{1.09}W_{0.7}K_{0.8}Sr_{0.1}Bi_{0.1}Se_{0.1}Cr_{0.1}Pd_{0.1}$ 1,000 ml of the catalyst (12) was filled into the material gas inlet portion of a steel-made reaction tube of 25.4 mm in inside diameter, and successively 500 ml of the catalyst (13) was filled into the outlet portion of the same reaction tube, to effect a reaction in the same manner as in Example 1.

The results are shown in Table 4.

EXAMPLE 14

To 40 l of heated deionized water were added 8,830 g of ammonium paramolybdate and 531.4 g of ammonium metavanadate. The resulting mixture was stirred to obtain a solution. To this solution were added 523.7 g of orthophosphoric acid (85 wt.%), an aqueous solution obtained by dissolving 812.3 g of cesium nitrate, 444 g of thallium nitrate, 121.2 g of nickel nitrate 119.6 g of manganese nitrate and 135.4 g of rhodium nitrate in 10 l of deionized water, 133 g of powdery tellurium dioxide and 166.2 g of powdery niobium pentoxide, in this order. The resulting mixture was heated with stirring, to effect aging.

In the resulting suspension as immersed 1,600 ml of a carrier consisting of ring-shaped silica-alumina of 6 mm in outside diameter, 5 mm in length and 3 mm in inside diameter (diameter of the through-hole formed in the length direction. The system was heated to a predetermined temperature with stirring, to allow the carrier to support the catalyst active component. The system was then calcined in an air current at 400° C. for 3 hours to obtain a supported catalyst (14).

The compound oxide of this catalyst (14) had the following composition when expressed as an atomic ratio excluding oxygen.

$Mo_{12}P_{1.0}V_{1.09}Cs_{1.0}Tl_{0.4}Nb_{0.3}Ni_{0.1}Mn_{0.1}Te_{0.2}Rh_{0.1}$

The amount of the compound oxide supported was 20 g per 100 ml of the carrier.

A slurry was prepared in the same manner as for the catalyst (14) except that the amount of thallium nitrate used was changed to 111 g and the amount of niobium pentoxide used was changed to 55.4 g. The subsequent procedure was the same as in Example 1 to obtain a pellet catalyst (15) of 5 mm in outside diameter and 6 mm in length.

The catalyst (15) had the following composition when expressed as in an atomic ratio excluding oxygen.

$Mo_{12}P_{1.09}V_{1.09}Cs_{1.0}Tl_{0.1}Nb_{0.1}Ni_{0.1}Mn_{0.1}Te_{0.2}Rh_{0.1}$ 1,000 ml of the catalyst (14) was filled into the material gas inlet portion of a steel-made reaction tube of 25.4 mm in inside diameter, and successively 500 ml of the catalyst (15) was filled into the outlet portion of the same reaction tube, to effect a reaction in the same manner as in Example 1.

The results are shown in Table 4.

TABLE 1

| | Filling of catalyst(s) Inlet portion/outlet portion | Reaction temperature (°C.) | ΔT (°C.) | Methacrolein conversion (mole %) | Methacrylic acid (mole %) Selectivity | Methacrylic acid (mole %) one-pass yield |
|---|---|---|---|---|---|---|
| Example 1 | Pellet catalyst (1)/pellet catalyst (2) | 290 | 14 | 81.8 | 77.5 | 63.4 |
| Comparative Example 1 | Single layer of pellet catalyst (1) | 290 | 14 | 70.1 | 79.2 | 55.5 |
| 2 | Single layer of pellet catalyst (2) | 290 | 25 | 90.6 | 69.1 | 62.6 |
| 3 | Single layer of pellet catalyst (3) | 290 | 19 | 82.6 | 73.9 | 61.0 |
| Example 2 | Ring catalyst (1)/ring catalyst (2) | 290 | 12 | 81.9 | 79.4 | 65.0 |
| Comparative Example 4 | Single layer of ring catalyst (1) | 290 | 12 | 70.4 | 81.0 | 57.0 |
| 5 | Single layer of ring catalyst (2) | 290 | 21 | 91.1 | 70.6 | 64.3 |
| 6 | Single layer of ring catalyst (3) | 290 | 16 | 82.9 | 75.6 | 62.7 |
| Example 3 | Ring catalyst (1)/pellet catalyst (2) | 290 | 13 | 81.7 | 79.0 | 64.1 |
| 4 | Same as above | 290 | 13 | 79.2 | 79.2 | 62.7 |
| Comparative Example 7 | Single layer of pellet catalyst (3) | 290 | 18 | 75.1 | 73.6 | 55.3 |
| Example 5 | Ring catalyst (1)/ring catalyst (2) | 300 | 12 | 82.3 | 79.3 | 65.3 |
| Comparative Example 8 | Single layer of ring catalyst (1) | 300 | 13 | 70.8 | 80.2 | 56.8 |
| 9 | Single layer of ring catalyst (3) | 300 | 17 | 82.2 | 75.0 | 61.7 |
| Example 6 | Ring catalyst (1)/ring catalyst (2) | 290 | 13 | 83.2 | 79.2 | 65.9 |
| Comparative Example 10 | Single layer of ring catalyst (1) | 290 | 14 | 72.5 | 79.7 | 57.8 |
| 11 | Single layer of ring catalyst (3) | 290 | 18 | 84.5 | 73.8 | 62.4 |

Notes:
Example 4 and Comparative Example 7 = results after 4,000 hours of continuous operation
Example 5, Comparative Example 8 and Comparative Example 9 = space velocity 1,200 hr$^{-1}$ → 1,500 hr$^{-1}$
Example 6, Comparative Example 10 and Comparative Example 11 = methacrolein concentration 3.5 vol. % → 4.0 vol. %

TABLE 2

| | Filling of catalyst Inlet portion/outlet portion | Reaction temperature (°C.) | ΔT (°C.) | Isobutyl aldehyde conversion (mole %) | Selectivity (mole %) Methacrylic acid | Selectivity (mole %) Methacrolein | Methacrylic acid one-pass yield (mole %) |
|---|---|---|---|---|---|---|---|
| Example 7 | Ring catalyst (1)/ring catlyst (2) | 280 | 18 | 100.0 | 65.5 | 12.7 | 65.5 |
| Comparative Example 12 | Single layer of ring catalyst (1) | 280 | 21 | 97.7 | 66.6 | 12.2 | 65.1 |
| 13 | Single layer of ring catalyst (3) | 280 | 23 | 100.0 | 63.1 | 11.8 | 63.1 |

TABLE 3

| | Filling of catalyst Inlet portion/outlet portion | Reaction temperature (°C.) | ΔT (°C.) | Isobutyl acid conversion (mole %) | Methacrylic acid selectivity (mole %) | Metahcrylic acid one-pass yield (mole %) |
|---|---|---|---|---|---|---|
| Example 8 | Ring catalyst (1)/ring catlyst (2) | 280 | 22 | 98.6 | 78.4 | 77.3 |
| Comparative Example 14 | Single layer of ring catalyst (1) | 280 | 28 | 95.1 | 80.0 | 76.1 |
| 15 | Single layer of ring catalyst (3) | 280 | 30 | 98.3 | 74.2 | 72.9 |

TABLE 4

| | Filling of catalyst(s) Inlet portion/outlet portion | Reaction temperature (°C.) | ΔT (°C.) | Methacrolein conversion (mole %) | Methacrylic acid (mole %) Selectivity | Methacrylic acid (mole %) One-pass yield |
|---|---|---|---|---|---|---|
| Example 9 | Pellet catalyst (4)/pellet catalyst (5) | 290 | 13 | 80.6 | 77.1 | 62.1 |
| 10 | Pellet catalyst (6)/pellet catalyst (7) | 290 | 14 | 81.3 | 77.9 | 63.3 |
| 11 | Ring catalyst (8)/pellet catalyst (9) | 290 | 12 | 82.7 | 78.9 | 65.3 |
| 12 | Ring catalyst (10)/pellet catalyst (11) | 290 | 11 | 85.8 | 78.3 | 67.2 |
| 13 | Supported spherical catalyst (12)/ pellet catalyst (13) | 290 | 9 | 80.3 | 76.8 | 61.7 |
| 14 | Supported ring catalyst (14)/ | 290 | 9 | 80.8 | 76.6 | 61.9 |

TABLE 4-continued

| Filling of catalyst(s) Inlet portion/outlet portion | Reaction temperature (°C.) | ΔT (°C.) | Methacrolein conversion (mole %) | Methacrylic acid (mole %) | |
|---|---|---|---|---|---|
| | | | | Selectivity | One-pass yield |
| pellet catalyst (14) | | | | | |

What is claimed is:

1. A process for producing methacrylic acid, which comprises filling a plurality of catalysts of different activities into a plurality of reaction zones which have been formed in each of the reaction tubes of a fixed bed multi-tubular reactor by dividing said reaction tube into two or more portions in the direction of tubular axis, so that the activity of catalyst is higher as the reaction zone is closer to the outlet of the reaction tube, and introducing into the reaction zones containing the catalysts at least one compound selected from methacrolein, isobutyl aldehyde and isobutyric acid to oxidize the at least one compound with molecular oxygen or a molecular oxygen-containing gas, characterized in that said catalyst are compound oxides represented by the following general formula (I)

$$Mo_a P_b A_c B_d C_e O_x \qquad (I)$$

wherein Mo represents molybdenum; P represents phosphorus; A represents at least one element selected from arsenic, antimony, germanium, bismuth, zirconium, selenium, cerium, copper, iron, chromium, nickel, manganese, cobalt, tin, silver, zinc, palladium, rhodium and tellurium; B represents at least one element selected from vanadium, tungsten, and niobium; C represents at least one element selected from alkali metals, alkaline earth metals and thallium; O represents oxygen; a, b, c, d, e and x represent the atom number of Mo, P, A, B, C and O, respectively; when a is 12, b is 0.5-4, c is 0.001-5, d is 0.001-4 and e is 0.001-4; and x is a value determined by the oxidation state of each element, and in that said process comprises (i) preparing a plurality of catalysts of different activities by changing the types and/or amounts of the A group elements in the general formula (I) and then filling the catalysts into the reaction zones of each reaction tube so that the activity of catalyst is higher as the reaction zone is closer to the outlet of the reaction tube, (ii) preparing a plurality of catalysts of different activities by changing the types and/or amounts of the B group elements in the general formula (I) and then filling the catalysts into the reaction zones of each reaction tube so that the activity of catalyst is higher as the reaction zone is closer to the outlet of the reaction tube, or (iii) preparing a plurality of catalysts of different activities by changing the types and/or amounts of the elements of at least two groups selected from the A group, the B group and the C group in the general formula (I) and then filling the catalysts into the reaction zones of each reaction tube so that the activity of catalyst is higher as the reaction zone is closer to the outlet of the reaction tube.

2. The process according to claim 1, wherein the number of the reaction zones is 2 or 3.

3. The process according to claim 1, wherein the catalysts have a ring shape with a through-hole in its length direction, and an outside diameter of 3-10 mm, a length of 0.5-2 times the outside diameter and an inside diameter (the diameter of the through-hole) of 0.1-0.7 times the outside diameter.

* * * * *